(12) United States Patent
Todaro et al.

(10) Patent No.: US 12,004,576 B2
(45) Date of Patent: Jun. 11, 2024

(54) GARMENT WITH ABSORBENT PADS AND METHOD OF MANUFACTURE THEREOF

(71) Applicant: Mast Industries (Far East) Limited, Kowloon (HK)

(72) Inventors: Ursula Giovanna Todaro, Glendale, NY (US); Suet Hing Yip, Tai Wai (HK); Ka Lai Tam, Shatin New Town (HK); Jennifer Ostroski, Red Bank, NJ (US); Chang Ming Liang, Kwai Chung (HK)

(73) Assignee: Mast Industries (Far East) Limited, Kowloon (HK)

( * ) Notice: Subject to any disclaimer, the term of this patent is extended or adjusted under 35 U.S.C. 154(b) by 79 days.

(21) Appl. No.: 18/052,259

(22) Filed: Nov. 3, 2022

(65) Prior Publication Data

US 2023/0148686 A1    May 18, 2023

Related U.S. Application Data

(60) Provisional application No. 63/278,684, filed on Nov. 12, 2021.

(51) Int. Cl.
*A41C 3/14* (2006.01)
*A61F 13/14* (2006.01)

(52) U.S. Cl.
CPC ............ *A41C 3/144* (2013.01); *A61F 13/141* (2013.01)

(58) Field of Classification Search
CPC .............................. A41C 3/144; A61F 13/141
See application file for complete search history.

(56) References Cited

U.S. PATENT DOCUMENTS 1,895,861 A    1/1933  Albert
2,614,954 A   10/1952  Henry et al.
(Continued)

FOREIGN PATENT DOCUMENTS

CN    203341019 U    12/2013
CN    105249551 A     1/2016
(Continued)

OTHER PUBLICATIONS

International Search Report and Written Opinion in PCT/IB2022/060615, dated Jan. 30, 2023, 10 pages.
(Continued)

*Primary Examiner* — Gloria M Hale
(74) *Attorney, Agent, or Firm* — Andrus Intellectual Property Law, LLP

(57) ABSTRACT

An absorbent garment has a pair of breast cups, each having a layer of moisture-wicking one-way transport material, an inner layer of absorbent terry cloth, an inner layer of foam, and an outer layer of water-resistant material. An inner face of the absorbent terry cloth is fully laminated to an outer face of the one-way transport material. An outer face of the absorbent terry cloth is fully laminated to an inner face of the foam. An outer edge of the one-way transport material is coupled to an outer edge of the foam. An outer face of the foam is fully laminated to an inner face of the water-resistant material. The absorbent terry cloth has an outer edge that does not extend to the outer edges of the one-way transport material or the foam such that the absorbent terry cloth is fully enclosed between the one-way transport material and the foam.

20 Claims, 4 Drawing Sheets

(56) References Cited

U.S. PATENT DOCUMENTS

| | | | |
|---|---|---|---|
| 4,875,492 | A | 10/1989 | Mitchell et al. |
| 5,149,336 | A * | 9/1992 | Clarke .................. A61F 13/141 |
| | | | 604/385.07 |
| 5,269,720 | A | 12/1993 | Moretz et al. |
| 6,346,027 | B1 | 2/2002 | Merkovsky |
| 7,300,331 | B2 | 11/2007 | Baran et al. |
| 8,075,369 | B2 | 12/2011 | Hendrickson |
| 8,225,468 | B2 | 7/2012 | Wanzenboeck |
| 8,708,771 | B1 | 4/2014 | De Rosa |
| 10,117,785 | B2 | 11/2018 | Marquez |
| 10,231,491 | B2 | 3/2019 | Akerson et al. |
| 10,412,998 | B2 * | 9/2019 | Hinnershitz ........... A41D 1/215 |
| 10,413,452 | B2 | 9/2019 | Estevanell |
| 10,441,479 | B2 | 10/2019 | Griffiths |
| 10,441,480 | B2 | 10/2019 | Griffiths |
| 10,757,984 | B2 | 9/2020 | Akerson et al. |
| 10,786,016 | B2 * | 9/2020 | Caden ..................... A61F 13/14 |
| 11,154,431 | B1 | 10/2021 | Yip et al. |
| 2005/0004542 | A1 * | 1/2005 | Bakkila ................ A47G 23/032 |
| | | | 604/367 |
| 2010/0035514 | A1 | 2/2010 | Wong et al. |
| 2010/0121300 | A1 * | 5/2010 | Hann .................... A61F 13/141 |
| | | | 604/385.07 |
| 2013/0066288 | A1 | 3/2013 | Lin |
| 2013/0316615 | A1 * | 11/2013 | Hurd .................... A41D 31/125 |
| | | | 264/45.3 |
| 2019/0142992 | A1 | 5/2019 | Davidson et al. |
| 2020/0107589 | A1 | 4/2020 | McKinley |
| 2020/0222256 | A1 | 7/2020 | Chong |
| 2020/0375817 | A9 | 12/2020 | Griffiths |
| 2020/0383393 | A1 * | 12/2020 | Caden ..................... B32B 27/40 |
| 2021/0206144 | A1 | 7/2021 | Ewell |

FOREIGN PATENT DOCUMENTS

| | | |
|---|---|---|
| CN | 205161922 U | 4/2016 |
| CN | 205359802 U | 7/2016 |
| CN | 106109093 A | 11/2016 |
| CN | 206390312 U | 8/2017 |
| CN | 107156936 A | 9/2017 |
| CN | 206714890 U | 12/2017 |
| CN | 107811760 A | 3/2018 |
| CN | 107857836 A | 3/2018 |
| CN | 207383553 U | 5/2018 |
| CN | 207804479 U | 9/2018 |
| CN | 208002990 U | 10/2018 |
| CN | 108976444 A | 12/2018 |
| CN | 208193218 U | 12/2018 |
| CN | 208301801 U | 1/2019 |
| CN | 109350364 A | 2/2019 |
| CN | 208492495 U | 2/2019 |
| CN | 208626012 U | 3/2019 |
| CN | 208677736 U | 4/2019 |
| CN | 208693609 U | 4/2019 |
| CN | 209154226 U | 7/2019 |
| CN | 209426307 U | 9/2019 |
| CN | 209645233 U | 11/2019 |
| CN | 209677386 U | 11/2019 |
| CN | 209678861 U | 11/2019 |
| CN | 209695557 U | 11/2019 |
| CN | 210809344 U | 6/2020 |
| CN | 210988270 U | 7/2020 |
| CN | 211300675 U | 8/2020 |
| CN | 216059261 U | 3/2022 |
| DE | 20210029 U1 | 10/2002 |
| EP | 2816987 B1 | 6/2016 |
| GB | 2577982 A | 4/2020 |
| JP | 2009-68141 A | 4/2009 |
| KR | 10-2020-0089963 A | 7/2020 |
| WO | 2005034824 A1 | 4/2005 |
| WO | 2008029220 A2 | 3/2008 |
| WO | 2013123952 A1 | 8/2013 |
| WO | 2017192049 A1 | 11/2017 |
| WO | 2018234719 A1 | 12/2018 |
| WO | 2021118455 A1 | 6/2021 |

OTHER PUBLICATIONS

Victoria's Secret, "Victoria's Secret Bare Seamless Nursing Bra," Sep. 15, 2022, available at https://www.victoriassecret.com/us/vs/bras-catalog/5000008694?brand=vs&choice=54A2&genericid=11207252&recommendedProductType=IpProductRec1.

Declaration of Prior Art of Inventors Suet Hing Yip and Ka Lai Tam.

* cited by examiner

GARMENT WITH ABSORBENT PADS AND METHOD OF MANUFACTURE THEREOF

CROSS-REFERENCE TO RELATED APPLICATION

This application claims the benefit of U.S. Provisional Application Ser. No. 63/278,684, filed on Nov. 12, 2021, which is hereby incorporated by reference herein in its entirety.

FIELD

The present disclosure generally relates to bras specifically for maternity or nursing.

BACKGROUND

The following U.S. Patents and Applications provide background information.

U.S. Pat. No. 10,117,785 discloses a breast milk absorbing system including a nursing garment being that may be worn by a nursing female. The nursing garment has a pouch. An absorbing unit is provided. The absorbing unit is removably positioned within the pouch. The absorbing may absorb breast milk from the nursing female. Thus, the nursing garment is inhibited from becoming wet with the breast milk. The absorbing unit extends across an entire width of the pouch. Thus, the absorbing unit remains aligned with the nursing female's breasts.

U.S. Pat. No. 10,412,998 discloses a nursing garment that includes a back portion comprising a back layer; and a front portion coupled to the back portion. The front portion includes an external layer; a first middle layer that includes a leak-resistant fabric having at least one edge that is cut on the bias; a second middle layer that includes an absorbent material; and an innermost layer configured to be in contact with a nipple of a user, wherein the innermost layer includes a fabric configured to wick moisture away from the nipple of the user. The external layer, the first middle layer, the second middle layer and the innermost layer are coupled together such that the first middle layer extends between the external layer and the second middle layer, and the second middle layer extends between the first middle layer and the innermost layer.

U.S. Pat. No. 10,786,016 discloses undergarments that that are uniquely constructed to absorb fluids, such as those associated with sweat and lactation, in either prescribed areas of the undergarment or throughout the totality thereof.

U.S. Patent Application Publication No. 2020/0222256 discloses a protective insert operatively attachable to an inner, body-facing layer of a garment. The protective insert generally comprises, a first, operatively inner layer comprising a moisture-wicking, odor resistance, fluid absorbent fiber with or without a waterproof laminate-film; and a second, operatively outer layer comprising a breathable, odor resistant, water repellent fiber to further prevent fluid passage through the garment; wherein the operatively inner layer faces the body of a user while the operatively outer layer faces away from the body of a user, in use.

United Kingdom Patent No. 2577982 discloses a launderable nursing garment comprising a main body comprising a front portion comprising an outward-facing layer and a plurality of nipple shields, wherein each nipple shield comprises an absorbent system and a barrier layer. The barrier layer is positioned between the absorbent system and the outward-facing layer. The plurality of nipple shields is permanently attached to the outward-facing layer. The garment is a sleep bra. When the garment is worn by a user, the garment is movable form a first configuration in which both of the user's nipples are covered by the plurality of nipple shields to a second configuration in which one the user's nipples is covered by one of the plurality of nipple shields and the other of the user's nipples is not covered by the garment, wherein said movement does not require the opening of any fasteners of other closure mechanisms.

International Patent Application Publication No. 2017/192049 discloses both cups of a non-rigid brassiere or bra include four layers: elastic wicking material, absorbent material, a waterproofed layer of textile impregnated with a laundering-resistant, low-contact-angle fluoropolymer, and a decorative exterior. The treated textile has a barely altered permeability to gas including water vapor, and blocks all flow of aqueous liquid. Variations include nursing or non-ursing types of: absorbent bra, exercise bra, and sports top. Nursing bras have a "shutter frame' aperture having elastic edges, so the breast can be exposed to a variable extent when nursing. The elastic edges may slide over each other, being not directly attached.

International Patent Application Publication No. 2018/234719 discloses a washable multilayer nursing pad, comprising an edge and successive layers: —a knitted mesh layer at least 1.5 mm thick and perforated, comprising a top face in direct contact with the skin and a bottom face; —a layer of non-woven fibers, in contact with the top face, capable of absorbing at least 2.5 L/m2 of water; —a microporous layer comprising an impermeable and breathable structure; —a protective layer covering the entire microporous layer.

Chinese Utility Model No. 216059261 discloses a nursing bra which comprises a bra body convenient for a puerpera to wear, two ends of the bra body are fastened and fixed, two shoulder straps are arranged on the bra body, one end of each shoulder strap is provided with a male buckle, the bra body is provided with a female buckle detachably clamped with the male buckle, and the female buckle is connected with the female buckle. The bra body comprises a cotton cup surface layer, a cotton cup middle layer and a cotton cup inner layer, the cotton cup surface layer, the cotton cup middle layer and the cotton cup inner layer are subjected to die forming under corresponding dies, the cotton cup inner layer can conduct water to the cotton cup middle layer, and the cotton cup surface layer is used for preventing the water of the cotton cup middle layer from seeping out. According to the nursing bra, the two ends of the bra body are buckled and fixed, a puerpera can conveniently wear the bra, the male buckle and the female buckle are detachably clamped, the bra can be conveniently unfastened, and the nursing performance of the nursing bra is improved.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure relates to various examples of an absorbent garment comprising a pair of breast cups. Each breast cup in the pair of breast cups comprises a layer of moisture-wicking one-way transport material configured to face a wearer's skin when the garment is worn, an inner layer of absorbent terry cloth, an inner layer of foam, and an outer layer of water-resistant material. An inner face of the absorbent terry cloth is fully laminated to an outer face of the one-way transport material and an outer face of the absorbent terry cloth is fully laminated to an inner face of the foam. An outer edge of the one-way transport material is coupled to an outer edge of the foam. An outer face of the foam is fully laminated to an inner face of the water-resistant material. The absorbent terry cloth has an outer edge that does not extend to the outer edge of the one-way transport material nor to the outer edge of the foam such that the absorbent terry cloth is fully enclosed between the one-way transport material on the inner face thereof and the foam and the water-resistant material on the outer face thereof.

In one example, the one-way transport material is a lightweight rib jacquard fabric. Optionally, the one-way transport material weighs no more than 110 gsm.

In one example, the outer edge of the absorbent terry cloth is spaced inwardly from the respective outer edges of the one-way transport material and the foam by a predetermined offset. Optionally, the one-way transport material is bonded directly to the foam across an entire width of the predetermined offset.

In one example, the inner face of the absorbent terry cloth is smooth and the outer face of the absorbent terry cloth is fleecy.

In one example, the foam is an open-cell stretch foam.

In one example, the water-resistant material comprises fabric treated with a hydrophobic finish.

In one example, the outer edge of the one-way transport material is bonded directly to the outer edge of the foam.

In one example, the absorbent terry cloth is fully laminated to the one-way transport material and to the foam using hot melt spray glue.

In one example, the garment further comprises a pair of wings. A first wing in the pair of wings is stitched to a first breast cup in the pair of breast cups along the outer edge of the one-way transport material and the outer edge of the foam of the first breast cup, and the stitching does not go through the absorbent terry cloth of the first breast cup. A second wing in the pair of wings is stitched to a second breast cup in the pair of breast cups along the outer edge of the one-way transport material and the outer edge of the foam of the second breast cup, and the stitching does not go through the absorbent terry cloth of the second breast cup.

The present disclosure also relates to various examples of methods of manufacturing an absorbent breast cup. The method comprises providing a layer of moisture-wicking one-way transport material; providing a layer of absorbent terry cloth having an outer edge which does not extend to an outer edge of the one-way transport material when the absorbent terry cloth is centered on the one-way transport material; and fully laminating an inner face of the absorbent terry cloth to an outer face of the one-way transport material. The method includes providing a layer of foam having an outer edge which extends at least beyond the outer edge of the absorbent terry cloth when the foam is centered on the absorbent terry cloth; providing a layer of water-resistant material and fully laminating an inner face of the water-resistant material to an outer face of the foam. The method also comprises fully laminating an inner face of the foam to an outer face of the absorbent terry cloth and to the outer edge of the outer face of the one-way transport material that extends beyond the outer edge of the absorbent terry cloth. The method includes molding the one-way transport material, absorbent terry cloth, foam, and water-resistant material into a breast cup geometry such that the one-way transport material is configured to face a wearer's skin when the breast cup is worn.

In one example, the method includes sizing and shaping the absorbent terry cloth such that the outer edge of the absorbent terry cloth is spaced from the outer edge of the one-way transport material by a predetermined offset when the absorbent terry cloth is centered on the one-way transport material. Optionally, the inner layer of foam has the same size and shape as the one-way transport material, and the inner face of the foam is bonded directly to the outer face of the one-way transport material that extends beyond the outer edge of the absorbent terry cloth across an entire width of the predetermined offset.

In one example, the one-way transport material is a lightweight rib jacquard fabric. Optionally, the one-way transport material weighs no more than 110 gsm.

In one example, the method further comprises orienting the absorbent terry cloth in the breast cup such that the inner face of the absorbent terry cloth is smooth and the outer face of the absorbent terry cloth is fleecy.

In one example, the foam is an open-cell stretch foam.

In one example, the method further comprises treating a fabric with a hydrophobic finish to form the water-resistant material.

In one example, the method further comprises using hot melt spray glue to laminate the inner face of the water-resistant material to the outer face of the foam, to laminate the inner face of the foam to the outer face of the absorbent terry cloth and to the outer edge of the outer face of the one-way transport material, and to laminate the inner face of the absorbent terry cloth to the outer face of the one-way transport material.

In one example, in the molded breast cup, the absorbent terry cloth is fully enclosed between the one-way transport material on the inner face thereof and the foam and the water-resistant material on the outer face thereof.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The present application relates to garments, and more specifically to garments having a pair of absorbent breast cups, which are capable of absorbing bodily fluids such as breastmilk or sweat. Examples of such garments are bras, camisoles, swimsuits, and other similar upper torso garments including integral breast cups or adapted to receive insertable breast cups. The upper torso garments can be any size, shape, or style, which details are not limiting on the scope of the present disclosure.

Figure 1:
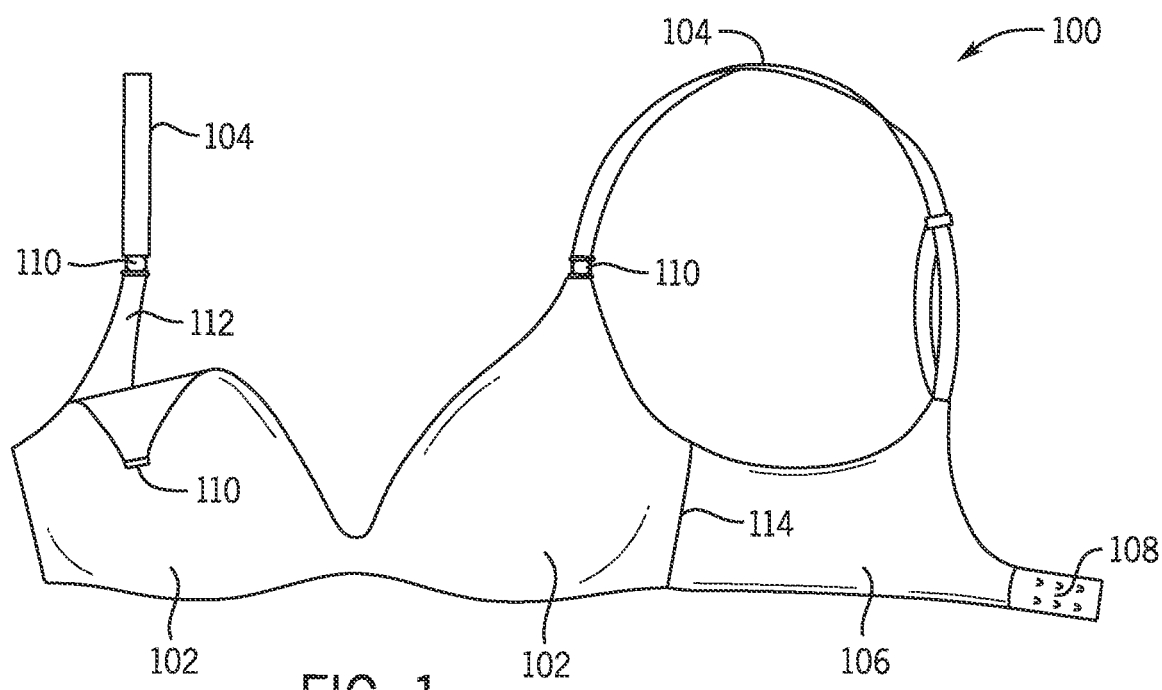
FIG. 1 illustrates a front view of a first example of a bra according to the present disclosure.

FIG. 1 shows a front view of one example of an absorbent bra 100. Here the bra 100 has two cups 102 and two shoulder straps 104 connected to respective upper edges of the cups 102. The rear end of each shoulder strap 104 is connected to a respective wing 106 (only one of which is shown), which wings 106 are attached to the outer edges of the cups 102 and are configured to encircle the wearer's torso. The wings 106 are connected in the back of the bra 100 by way of a hook and eye closure (part of which is shown at 108), as is conventional. As is also conventional for a nursing bra, the cups 102 are coupled at their upper edges to the shoulder straps 104 by way of clasps 110. This way, each cup 102 can be independently unclasped and folded down to allow access to the wearer's nipple for nursing. Slings (only one of which is shown at 112) connect to the lower front ends of the shoulder straps 104 and to the respective outer lower edges of the cups 102 so as to maintain the shoulder straps 104 in place while the cups 102 are folded down.

Figure 2:
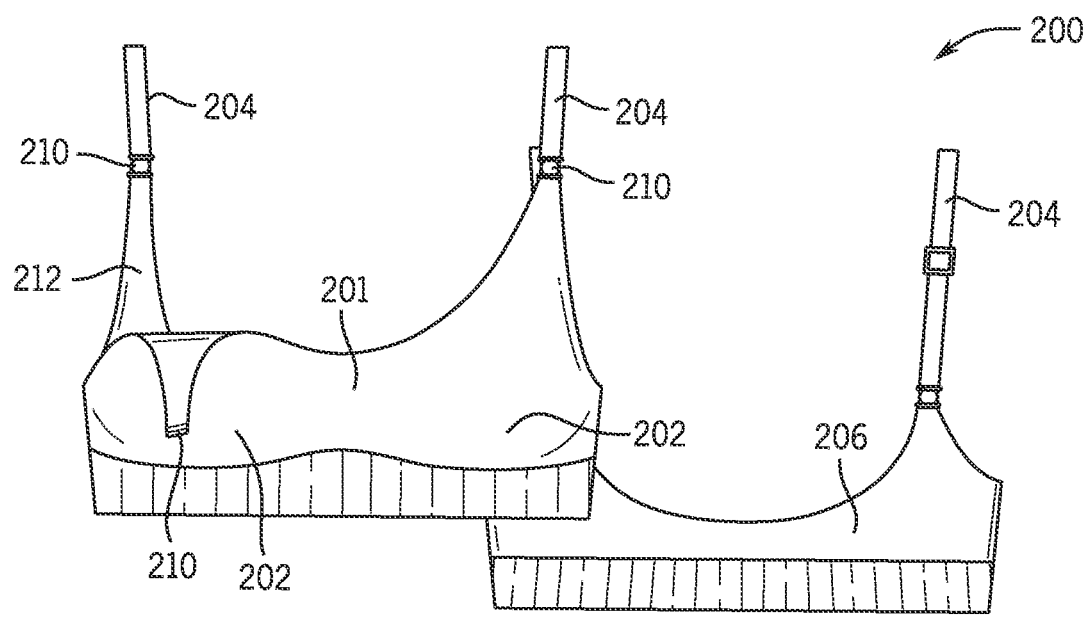
FIG. 2 illustrates front and back views of a second example of a bra according to the present disclosure.

FIG. 2 illustrates a second example of a bra 200 according to the present disclosure. The bra 200 has a front panel 201 with two cup areas 202 and a back band 206 that connects the opposite sides of the front panel 201. Shoulder straps 204 connect the tops of the cup areas 202 to the back band 206. The cup areas 202 are able to be folded down independently or together after being unclasped (at clasps 210) from the shoulder straps 204. Slings (only one of which is shown at 212) connect to the lower front ends of the shoulder straps 204 and to a lower edge of the front panel 201 so as to maintain the shoulder straps 204 in place while the cup areas 202 are folded down. The front panel 201 may have an inner (skin-touching) layer of liner material with a slit or slits (not shown) therein to allow for insertion and removal of removable absorbent breast cups between the outer layer of the front panel 201 shown in FIG. 2 and the inner liner layer. Such slits are well known for use in bras with removable pads and can be located at the underarm areas, at the lower ends of the cup areas 202, or at the neckline of the bra 200. The layer of liner material may be a mesh or another type of permeable material through which liquid is efficiently transported such that the liquid can be pulled away from the wearer's skin and absorbed by the removable breast cups.

Figure 3:
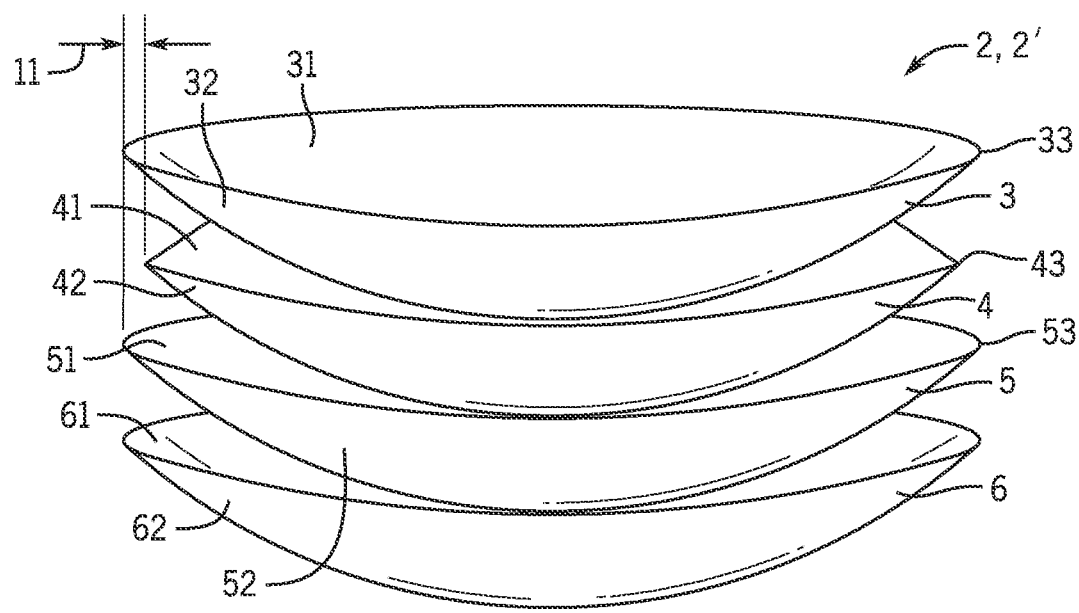
FIG. 3 is an exploded view of layers of a breast cup according to the present disclosure.

FIG. 3 shows an exploded view of the layers of an absorbent breast cup 2. The skin-facing layer is a moisture-wicking one-way transport material 3 and is in contact with an inner layer of absorbent terry cloth 4. Opposite the one-way transport material 3 and in contact with the opposing face of the absorbent terry cloth 4 is an inner layer of foam 5. An outer layer of water-resistant material 6 is pictured in contact with the inner layer of foam 5 opposite the absorbent terry cloth 4. The inner layer of absorbent terry cloth 4 is fully laminated on inner and outer faces 41, 42 thereof to the one-way transport material 3 and the foam 5, respectively. An outer edge 33 of the outer face 32 of the one-way transport material 3 is coupled to an outer edge 53 of the inner face 51 of the foam 5. In a preferred embodiment, the outer edge 33 of the one-way transport material 3 is bonded to the outer edge 53 of the foam 5 using a hot melt spray glue. Alternative methods of coupling include stitching, elastomeric heat-activated adhesive tape/film (such as that available from BEMIS™), spray adhesive, printed adhesive, mesh adhesive tape, ultrasonic bonding, and/or liquid glue.

As noted, the exemplary embodiment of the disclosure requires that the absorbent terry cloth 4 is fully laminated on its inner and outer faces 41, 42 to the one-way transport material 3 and the foam 5, respectively. In one example, the absorbent terry cloth 4 is fully laminated to the one-way transport material 3 and to the foam 5 using hot melt spray glue. Fully laminating the absorbent terry cloth 4 to the one-way transport material 3 controls the movement of liquid through the layers because they are in direct contact with one another across the entire inner face 41 face of the absorbent terry cloth 4. Full lamination of the outer face 42 of the absorbent terry cloth 4 to the inner face 51 of the foam 5 ensures that a majority of the liquid is absorbed by the absorbent terry cloth 4 before the liquid absorbs into the foam 5. In other embodiments, the absorbent terry cloth 4 may be laminated only at an outer edge 43 thereof to the one-way transport material 3 and the foam 5; however, this may result in less controlled movement of the liquid from the one-way transport material 3 to the absorbent terry cloth 4, as the two layers would be able to move (e.g., float, slip, or slide) with respect to one another.

Figure 4:
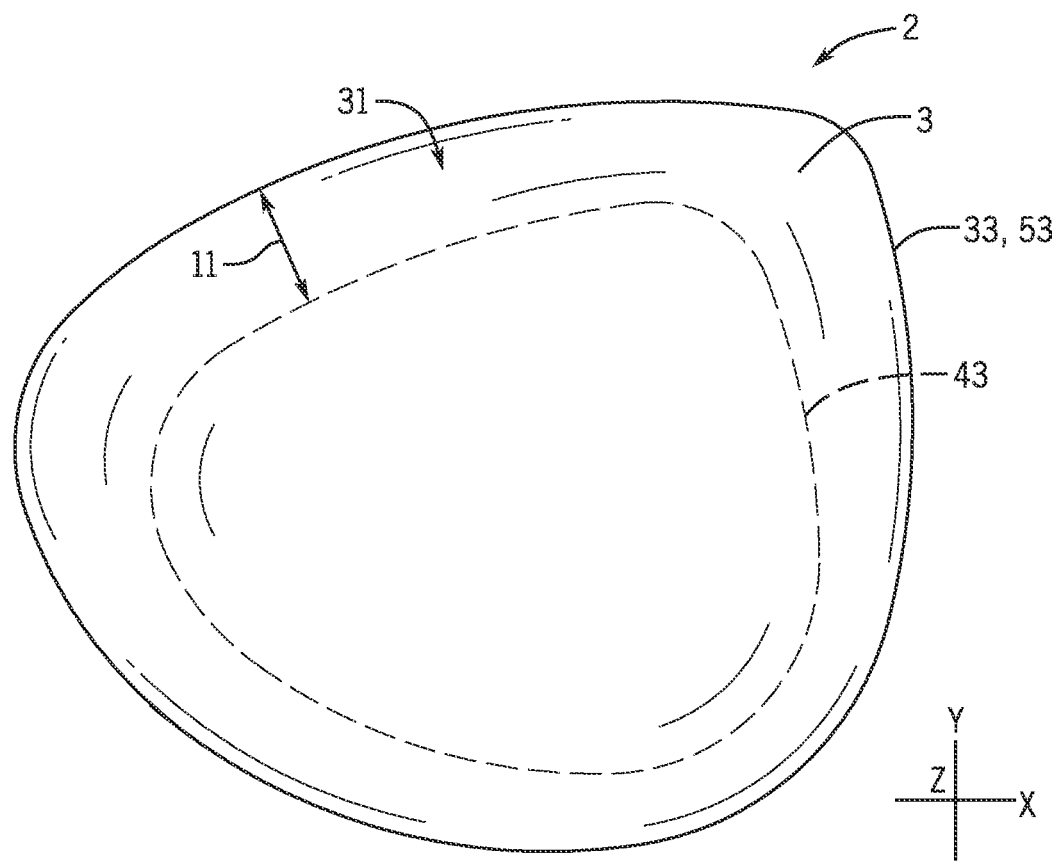
FIG. 4 illustrates a view of an absorbent breast cup from an inner face thereof, wherein the breast cup is configured to be removable from a brassiere.
Figure 5:
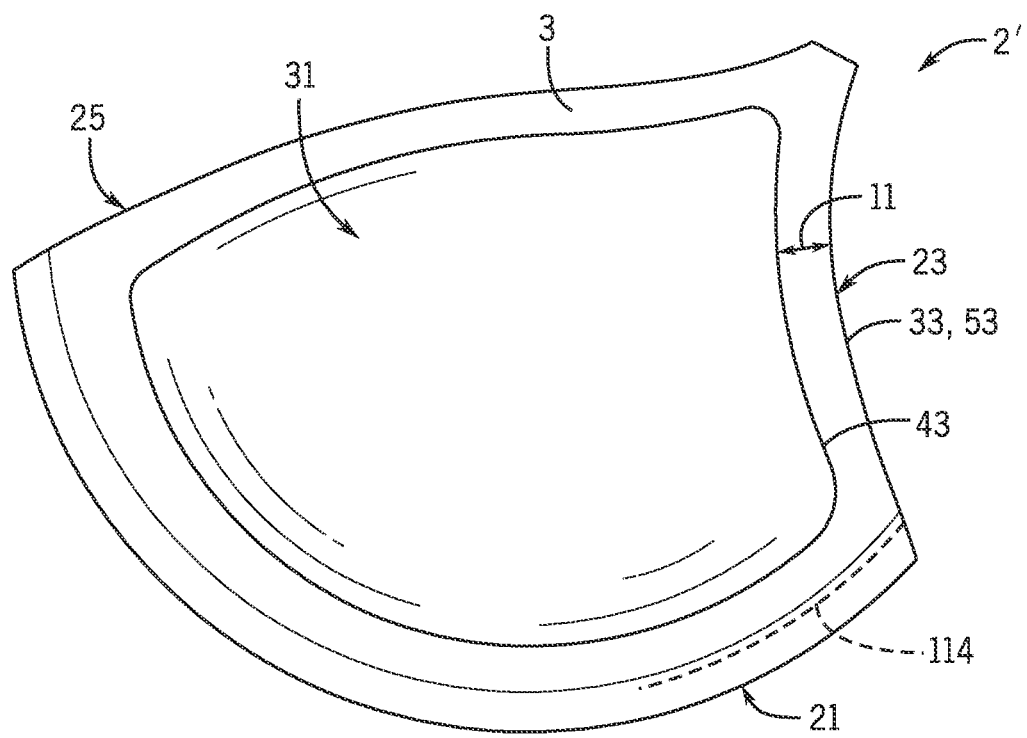
FIG. 5 illustrates a view of an absorbent breast cup from an inner face thereof, wherein the breast cup is configured to be sewn into a brassiere.
Figure 6:
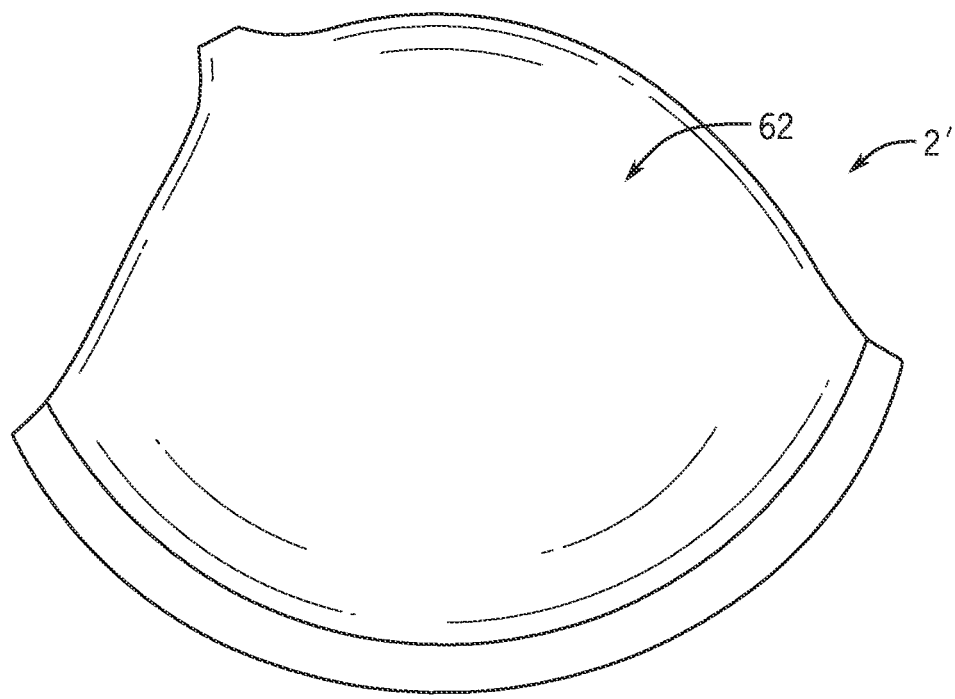
FIG. 6 illustrates an outer view of the breast cup of FIG. 5.

FIGS. 4-6 show views of various embodiments of absorbent breast cups 2, 2' in their assembled forms. FIGS. 4 and 5 show views of the inside faces of the breast cups 2, 2', which would be in contact with or at least facing the wearer's skin when the breast cup 2, 2' is worn. FIG. 6 shows the outside face of the breast cup 2' of FIG. 5. Two of the breast cups 2 of FIG. 4 could be used as removable pads insertable between the inner liner layer and outer layer of the front panel 201 of the bra 200 of FIG. 2, while two of the breast cups 2' of FIGS. 5 and 6 could be used as the cups 102 in the bra 100 of FIG. 1. Thus, taken together, FIGS. 1-6 show examples of an absorbent garment (e.g., bras 100, 200) comprising a pair of breast cups 2, 2'. Each breast cup 2, 2' in the pair of breast cups comprises a layer of moisture-wicking one-way transport material 3 configured to face a wearer's skin when the garment 100, 200 is worn, an inner layer of absorbent terry cloth 4, an inner layer of foam 5, and an outer layer of water-resistant material 6. An inner face 41 of the absorbent terry cloth 4 is fully laminated to an outer face 32 of the one-way transport material 3 and an outer face 42 of the absorbent terry cloth 4 is fully laminated to an inner face 51 of the foam 5. An outer edge 33 of the one-way transport material 3 is coupled to an outer edge 53 of the foam 5. An outer face 52 of the foam 5 is fully laminated to an inner face 61 of the water-resistant material 6. The absorbent terry cloth 4 has an outer edge 43 that does not extend to the outer edge 33 of the one-way transport material 3 nor to the outer edge 53 of the foam 5 such that the absorbent terry cloth 4 is fully enclosed between the one-way transport material 3 on the inner face 41 thereof and the foam 5 and the water-resistant material 6 on the outer face 42 thereof.

It is a feature of the preferred embodiment that the layer of absorbent terry cloth 4 has an outer edge 43 that does not extend to the outer edge 33 of the one-way transport material 3 nor to the outer edge 53 of the foam 5 when the layers 3, 4, 5 are centered with respect to one another (i.e., aligned one on top of the other with their perimeters being concentric) such that the absorbent terry cloth 4 is fully enclosed between the one-way transport material 3 and the foam 5 around its entire perimeter. This way, liquid that is absorbed by the absorbent terry cloth 4 is sealed within the breast cup 2, 2' by the adhesive in the bonded edge of the breast cup 2, 2', where the outer edge 33 of the one-way transport material 3 is bonded directly to the outer edge 53 of the foam 5. In some embodiments, the outer edge 43 of the absorbent terry cloth 4 is spaced inwardly from the respective outer edges 33, 53 of the one-way transport material 3 and the foam 5 by a predetermined offset 11. When the foam 5 is laminated to the absorbent terry cloth 4 and to the outer edge 33 of the one-way transport material 3, the one-way transport material 3 is bonded directly to the foam 5 across an entire width of the predetermined offset 11. In one example, the predetermined offset 11 has a width between about 0.5 cm and 1.5 cm. Note that the predetermined offset 11 may have roughly the same width around the entire perimeter of the breast cup 2 as shown in FIG. 4, or may vary in width as shown in FIG. 5 (e.g., the offset at the bottom edge 21 of the breast cup 2' is greater than the offset at the underarm edge 23 or the neckline edge 25 of the breast cup 2'). In general, the absorbent terry cloth 4 will have the same perimetral shape as the perimetral shape of the one-way transport material 3 and the foam 5, but the absorbent terry cloth 4 could have a different perimetral shape than that of the one-way transport material 3 and the foam 5 such that the offset 11 is irregular around the perimeter of the breast cup 2, 2'.

In an instance in which the breast cup is a floating breast cup 2 meant for insertion into the bra 200 of FIG. 2, lamination across the width of the predetermined offset 11 effectively creates an envelope for the absorbent terry cloth 4, preventing leaks out the edges of the breast cup 2. In an instance in which the breast cup is a breast cup 2' meant to be sewn into the bra 100 of FIG. 1, the offset 11 allows the outer edges of the breast cup 2' to be stitched to other bra components so as to incorporate the breast cup 2' into the cup 102 of the bra 100. For example, the breast cup 2' can be stitched to a wing 106 of the bra 100 along the line 114 at the bottom edge 21 thereof, which stitching at line 114 is fully within the laminated predetermined offset 11. Thus, according to one example, a garment (e.g., bra 100) of the present disclosure may further comprising a pair of wings 106. A first wing 106 in the pair of wings is stitched to a first breast cup 2' in the pair of breast cups along the outer edge 33 of the one-way transport material 3 and the outer edge 53 of the foam 5 of the first breast cup 2', wherein the stitching does not go through the absorbent terry cloth 4 of the first breast cup 2'. A second wing 106 in the pair of wings is stitched to a second breast cup 2' in the pair of breast cups along the outer edge 33 of the one-way transport material 3 and the outer edge 53 of the foam 5 of the second breast cup 2', wherein the stitching does not go through the absorbent terry cloth 4 of the second breast cup 2'. Furthermore, an outer liner layer of fabric can be folded over the breast cup 2' and sewn thereto along the underarm edge 23 and the neckline edge 25 of the breast cup 2', again with all stitching being within the predetermined offset 11. A cradle and/or center gore can also be sewn to the breast cup 2' with all stitching being within the laminated offset 11. Because all stitching that connects the breast cups 2' to other components of the bra 100 is done within the fully laminated offset 11, liquid is unlikely to leak from the edges of the breast cups 2'.

FIGS. 4-6 show embodiments of the breast cup layers wherein the shapes of the layers are oblong or teardrop shaped, but the breast cup 2, 2' could instead be an ovular or a circular shape (e.g., FIG. 3). The shapes disclosed are non-limiting and can be altered according to a preferred style and/or size of bra or other type of garment.

Figure 7:
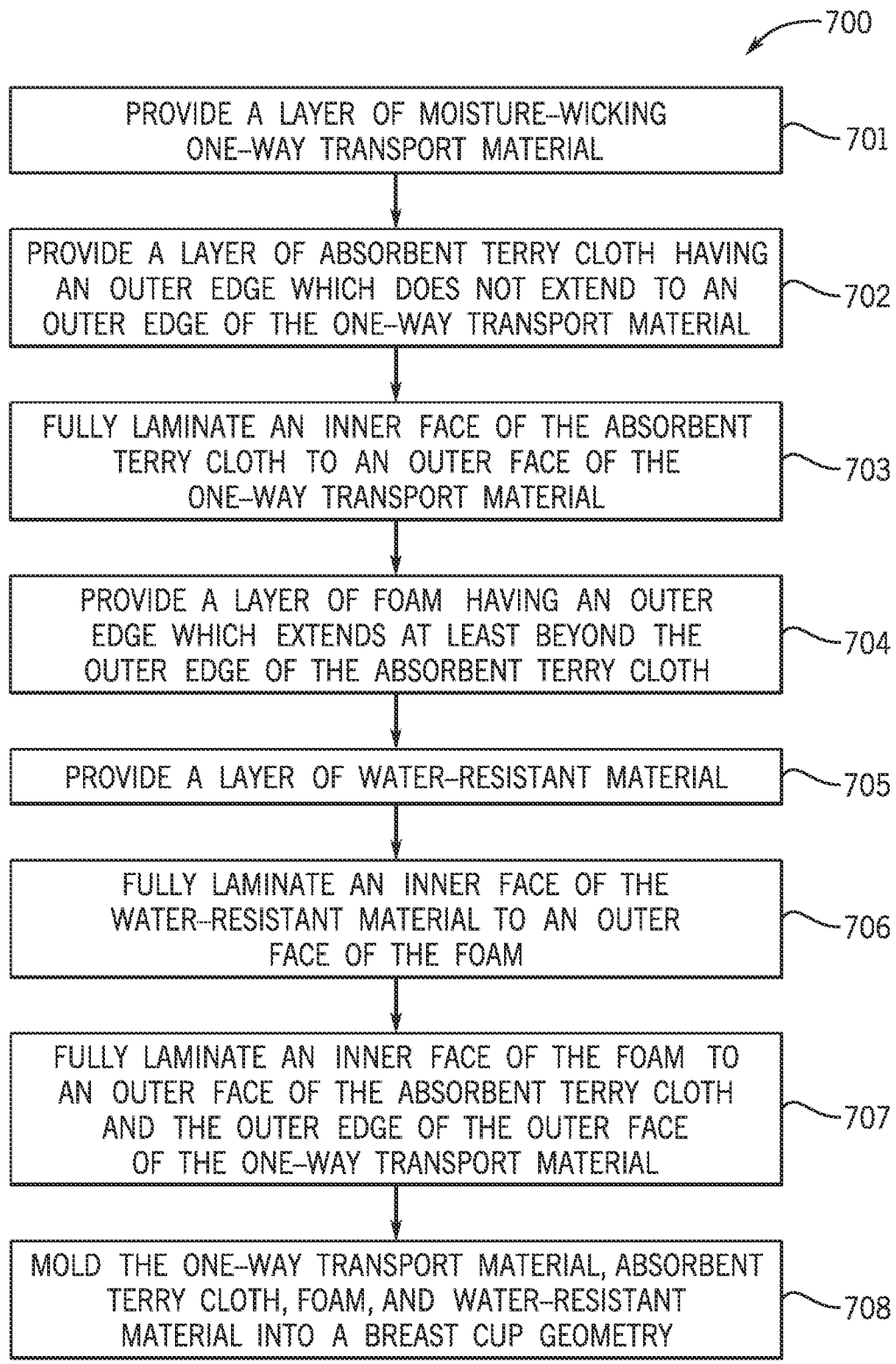
FIG. 7 illustrates a method for manufacturing a pair of absorbent breast cups.

FIG. 7 discloses a method 700 for manufacturing an absorbent breast cup 2, 2'. The method 700 comprises providing a layer of moisture-wicking one-way transport material 3 (step 701) and a layer of absorbent terry cloth 4 having an outer edge 43 which does not extend to an outer edge 33 of the one-way transport material 3 when the absorbent terry cloth 4 is centered on the one-way transport material 3 (step 702). As shown at step 703, the method includes fully laminating an inner face 41 of the absorbent terry cloth 4 to an outer face 32 of the one-way transport material 3, such as for example by applying spray glue or another type of adhesive on the entire inner face 41 of the absorbent terry cloth 4 and pressing the two layers together between rollers. At step 704, a layer of foam 5 is provided, which has an outer edge 53 which extends at least beyond the outer edge 43 of the absorbent terry cloth 4 when the foam 5 is centered on the absorbent terry cloth 4. At step 705, a layer of water-resistant material 6 is also provided. The method 700 further comprises fully laminating an inner face 61 of the water-resistant material 6 to an outer face 52 of the foam 5, as shown at step 706. This could be done, for example, by applying adhesive between the two layers 5, 6 and passing them between a pair of rollers, as is conventional. To combine the two laminated subassemblies and fully enclose the absorbent terry cloth 4, at step 707, an inner face 51 of the foam 5 is fully laminated to an outer face 42 of the absorbent terry cloth 4 and to the outer edge 33 of the outer face 32 of the one-way transport material 3 that extends beyond the outer edge 43 of the absorbent terry cloth 4. This could be done by coating the outer face 42 of the absorbent terry cloth 4 and the outer edge 33 of the one-way transport material 3 with adhesive, such as, for example, spray glue, placing the combined layers in a flat press, and applying heat. Finally, step 708 includes molding the one-way transport material 3, absorbent terry cloth 4, foam 5, and water-resistant material 6 into a breast cup geometry such that the one-way transport material 3 is configured to face a wearer's skin when the breast cup 2, 2' is worn. If necessary, the molded pad can then be trimmed to a desired size and shape using die-cutting.

In one example, the method 700 includes sizing and shaping the absorbent terry cloth 4 such that the outer edge 43 of the absorbent terry cloth 4 is spaced from the outer edge 33 of the one-way transport material 3 by a predetermined offset 11 when the absorbent terry cloth 4 is centered on the one-way transport material 3. Optionally, the inner layer of foam 5 has the same size and shape as the one-way transport material 3, and the inner face 51 of the foam 5 is bonded directly to the outer face 32 of the one-way transport material 3 that extends beyond the outer edge 43 of the absorbent terry cloth 4 across an entire width of the predetermined offset 11. In another example, the one-way transport material 3 has an outer edge 33 that extends beyond that of the outer edge 53 of the foam, and the outer edge 33 of the one-way transport material 3 can be folded over the outer edge 53 of the foam 5 and bonded or stitched to the foam 5 within the predetermined offset 11.

In one example, the method 700 further comprises orienting the absorbent terry cloth 4 in the breast cup 2, 2' such that the inner face 41 of the absorbent terry cloth 4 is smooth and the outer face 42 of the absorbent terry cloth 4 is fleecy.

In one example, the method 700 further comprises using hot melt spray glue to laminate the inner face 61 of the water-resistant material 6 to the outer face 52 of the foam 5, to laminate the inner face 51 of the foam 5 to the outer face 42 of the absorbent terry cloth 4 and to the outer edge 33 of the outer face 32 of the one-way transport material 3, and to laminate the inner face 41 of the absorbent terry cloth 4 to the outer face 32 of the one-way transport material 3.

In one example, in the molded breast cup 2, 2', the absorbent terry cloth 4 is fully enclosed between the one-way transport material 3 on the inner face 41 thereof and the foam 5 and the water-resistant material 6 on the outer face 42 thereof.

Returning to FIG. 3, the one-way transport material 3 is the innermost layer, with an inner face 31 configured to be in contact with or at least face the skin of the wearer when the breast cup is worn as part of a garment. The one-way transport material 3 can be any material that quickly absorbs liquid and pulls it away from the wearer's body. In one example, the one-way transport material 3 is a TurboDry™ fabric. TurboDry™ fabric is lightweight, weighing only about 95 gsm to about 110 gsm, as opposed to other push-pull materials which require at least 150 gsm to perform their function. In one example, the one-way transport material 3 comprising TurboDry™ fabric weighs no more than 110 gsm. In one particular example, the one-way transport material 3 is a TurboDry™ fabric that is an 87% polyester, 13% elastane rib jacquard fabric that weighs about 110 gsm. In another particular example, the one-way transport material 3 is a TurboDry™ fabric that is a 100% polyester rib jacquard fabric that weighs about 95 gsm. TurboDry™ fabric is knit specifically to have a surface contact angle against the skin that tends to pull moisture away from the skin in the z-direction (FIG. 4) by capillary action. Moisture may then spread in the x- and y-directions throughout and along the outer face 32 of the one-way transport material 3 that is configured to be located further from the wearer's skin, again by capillary action, such that the moisture is located on the outer face 32 of the one-way transport material 3 instead of the inner face 31 that contacts or faces the wearer's skin. In this regard, the one-way transport material 3 as a whole is considered to absorb water by capillary action, even if it is knit from yarns of a hydrophobic polymer, such as, for example, polyester. In another example, a push-pull effect of the one-way transport material 3 can be provided by yarn choice and fabric construction, such as if the inner face 31 of the one-way transport material 3 is constructed of yarn which is liquid-repellant and the outer face 32 is constructed of yarn that is liquid-absorbent. The liquid will be pushed by the liquid-repellant inner face 31 to go through to the liquid-absorbent outer face 32, which simultaneously pulls the water away from the skin-facing, liquid-repellant inner face 31 of the one-way transport material 3.

The layer of absorbent terry cloth 4 can be any appropriate terry material. In one example, the layer of absorbent terry cloth 4 is capable of absorbing at least 500%, and in some examples at least 570%, of its initial weight in water. In one particular example, a 5.67 square-inch sample of the absorbent terry cloth 4 can absorb on average about 7.5 milliliters of water. The layer of absorbent terry cloth 4 can be a double- or single-sided terry. The layer of absorbent terry cloth 4 can be French terry fabric, with the non-flat side being maintained as longer loops of yarn or being shredded to create fleece. In a preferred embodiment, the absorbent terry cloth 4 is a French terry, wherein the inner face 41 of the absorbent terry cloth 4 is smooth and the outer face 42 of the absorbent terry cloth 4 is fleecy. In one particular example, the layer of absorbent terry cloth 4 is weft-knit French terry, the non-flat side of which has been shredded to form fleece, made of 84% cotton (30S), 16% polyester (10S) having a weight of 340 gsm. In this configuration, the liquid is wicked away from the smooth inner face 41 of the absorbent terry cloth 4 toward the more absorbent fleecy outer face 42. In one example, the absorbent terry cloth 4 is treated on the outer face 42 with a chemical that causes the material to pull liquid away from its inner face 41 and thereafter prevents the liquid from returning to the inner face 41 of the material. In another example, the absorbent terry cloth 4 is a two-layer bonded terry or fleece fabric, the non-flat (e.g., fleecy) side of which is treated with a water-absorbent finish.

The layer of foam 5 can be any foam capable of providing a suitable padding according to the style of the bra 100, 200. In a preferred embodiment, the layer of foam 5 is an open-cell stretch foam having an element of water affinity.

FIG. 6 shows an outer view of the breast cup 2', showing the outer face 62 of the outer layer of water-resistant material 6. In certain embodiments, the water-resistant material 6 is a fabric treated with a hydrophobic finish. The fabric can be 100% polyester, 95 gsm interlock knit fabric. Preferably, the water-repellent finish is provided on the fabric before the water-resistant material 6 is laminated with the foam 5. If the breast cup 2' is to be sewn into a bra 100 like that of FIG. 1, this water-resistant material 6 can be covered with an outer liner layer of material for aesthetic purposes.

The bras 100, 200 and breast pads 2, 2' are washable and reusable without losing their functionality, such as their wicking capabilities, absorbency, water-resistance, breathability, shape, and construction integrity.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. An absorbent garment comprising:
   a pair of breast cups, each breast cup in the pair of breast cups comprising:
     a layer of moisture-wicking one-way transport material configured to face a wearer's skin when the garment is worn;
     an inner layer of absorbent terry cloth;
     an inner layer of foam; and
     an outer layer of water-resistant material;
   wherein an inner face of the absorbent terry cloth is fully laminated to an outer face of the one-way transport material and an outer face of the absorbent terry cloth is fully laminated to an inner face of the foam;
   wherein an outer edge of the one-way transport material is coupled to an outer edge of the foam;
   wherein an outer face of the foam is fully laminated to an inner face of the water-resistant material; and
   wherein the absorbent terry cloth has an outer edge that does not extend to the outer edge of the one-way transport material nor to the outer edge of the foam such that the absorbent terry cloth is fully enclosed between the one-way transport material on the inner face thereof and the foam and the water-resistant material on the outer face thereof.

2. The absorbent garment of claim 1, wherein the one-way transport material is a lightweight rib jacquard fabric.

3. The absorbent garment of claim 2, wherein the one-way transport material weighs no more than 110 gsm.

4. The absorbent garment of claim 1, wherein the outer edge of the absorbent terry cloth is spaced inwardly from the respective outer edges of the one-way transport material and the foam by a predetermined offset.

5. The absorbent garment of claim 4, wherein the one-way transport material is bonded directly to the foam across an entire width of the predetermined offset.

6. The absorbent garment of claim 1, wherein the inner face of the absorbent terry cloth is smooth and the outer face of the absorbent terry cloth is fleecy.

7. The absorbent garment of claim 1, wherein the foam is an open-cell stretch foam.

8. The absorbent garment of claim 1, wherein the water-resistant material comprises fabric treated with a hydrophobic finish.

9. The absorbent garment of claim 1, wherein the outer edge of the one-way transport material is bonded directly to the outer edge of the foam.

10. The absorbent garment of claim 1, wherein the absorbent terry cloth is fully laminated to the one-way transport material and to the foam using hot melt spray glue.

11. The absorbent garment of claim 1, further comprising a pair of wings;
   wherein a first wing in the pair of wings is stitched to a first breast cup in the pair of breast cups along the outer edge of the one-way transport material and the outer edge of the foam of the first breast cup, wherein the stitching does not go through the absorbent terry cloth of the first breast cup; and
   wherein a second wing in the pair of wings is stitched to a second breast cup in the pair of breast cups along the outer edge of the one-way transport material and the outer edge of the foam of the second breast cup, wherein the stitching does not go through the absorbent terry cloth of the second breast cup.

12. A method of manufacturing an absorbent breast cup, the method comprising:
   providing a layer of moisture-wicking one-way transport material;
   providing a layer of absorbent terry cloth having an outer edge which does not extend to an outer edge of the one-way transport material when the absorbent terry cloth is centered on the one-way transport material;
   fully laminating an inner face of the absorbent terry cloth to an outer face of the one-way transport material;
   providing a layer of foam having an outer edge which extends at least beyond the outer edge of the absorbent terry cloth when the foam is centered on the absorbent terry cloth;
   providing a layer of water-resistant material;
   fully laminating an inner face of the water-resistant material to an outer face of the foam;
   fully laminating an inner face of the foam to an outer face of the absorbent terry cloth and to the outer edge of the outer face of the one-way transport material that extends beyond the outer edge of the absorbent terry cloth; and
   molding the one-way transport material, absorbent terry cloth, foam, and water-resistant material into a breast cup geometry such that the one-way transport material is configured to face a wearer's skin when the breast cup is worn.

13. The method of claim 12, further comprising sizing and shaping the absorbent terry cloth such that the outer edge of the absorbent terry cloth is spaced from the outer edge of the one-way transport material by a predetermined offset when the absorbent terry cloth is centered on the one-way transport material.

14. The method of claim 13, wherein the inner layer of foam has the same size and shape as the one-way transport material, and the inner face of the foam is bonded directly to the outer face of the one-way transport material that extends beyond the outer edge of the absorbent terry cloth across an entire width of the predetermined offset.

15. The method of claim 12, wherein the one-way transport material is a lightweight rib jacquard fabric.

16. The method of claim 15, wherein the one-way transport material weighs no more than 110 gsm.

17. The method of claim 12, further comprising orienting the absorbent terry cloth in the breast cup such that the inner face of the absorbent terry cloth is smooth and the outer face of the absorbent terry cloth is fleecy.

18. The method of claim 12, wherein the foam is an open-cell stretch foam.

19. The method of claim 12, further comprising using hot melt spray glue to laminate the inner face of the water-resistant material to the outer face of the foam, to laminate the inner face of the foam to the outer face of the absorbent terry cloth and to the outer edge of the outer face of the one-way transport material, and to laminate the inner face of the absorbent terry cloth to the outer face of the one-way transport material.

20. The method of claim 12, wherein, in the molded breast cup, the absorbent terry cloth is fully enclosed between the one-way transport material on the inner face thereof and the foam and the water-resistant material on the outer face thereof.

* * * * *